US010514356B2

(12) United States Patent
Hino

(10) Patent No.: US 10,514,356 B2
(45) Date of Patent: Dec. 24, 2019

(54) GAS SENSOR

(71) Applicant: DENSO CORPORATION, Kariya, Aichi-pref. (JP)

(72) Inventor: Satoshi Hino, Kariya (JP)

(73) Assignee: DENSO CORPORATION, Kariya (JP)

( * ) Notice: Subject to any disclaimer, the term of this patent is extended or adjusted under 35 U.S.C. 154(b) by 101 days.

(21) Appl. No.: 15/852,102

(22) Filed: Dec. 22, 2017

(65) Prior Publication Data

US 2018/0180570 A1     Jun. 28, 2018

(30) Foreign Application Priority Data

Dec. 23, 2016   (JP) ................................ 2016-250260

(51) Int. Cl.
| | |
|---|---|
| *G01N 27/407* | (2006.01) |
| *G01N 27/406* | (2006.01) |
| *G01N 27/409* | (2006.01) |
| *G01N 27/41* | (2006.01) |
| *G01N 33/00* | (2006.01) |
| *G01N 27/416* | (2006.01) |

(Continued)

(52) U.S. Cl.
CPC ....... *G01N 27/4077* (2013.01); *G01N 27/409* (2013.01); *G01N 27/4062* (2013.01); *G01N 27/4078* (2013.01); *G01N 27/41* (2013.01); *G01N 33/0027* (2013.01); *G01N 27/4071* (2013.01); *G01N 27/4074* (2013.01); *G01N 27/416* (2013.01); *H01R 13/508* (2013.01); *H01R 13/6683* (2013.01)

(58) Field of Classification Search
None
See application file for complete search history.

(56) References Cited

U.S. PATENT DOCUMENTS 5,423,972 A * 6/1995 Mann .................. G01N 27/407
                                                                            204/424
2001/0025522 A1* 10/2001 Kojima .............. G01N 27/4071
                                                                             73/31.05

(Continued)

FOREIGN PATENT DOCUMENTS

| JP | 2002-131269 | † | 5/2002 |
| JP | 2002131269 A | * | 5/2002 |

(Continued)

*Primary Examiner* — Paul M. West
*Assistant Examiner* — Mark A Shabman
(74) *Attorney, Agent, or Firm* — Nixon & Vanderhye PC

(57) ABSTRACT

A gas sensor is provided which includes a sensor device, a plurality of contact springs, an insulator, a plurality of connecting terminals, and a lead cover. The insulator has an end surface which faces the connecting terminals and also includes as many protrusions as the contact springs. The insulator also has formed therein holding holes in which the contact springs are disposed. Each of the protrusions has formed therein a through-hole which communicates between an end surface of the protrusion and one of the holding holes. The through-holes are discrete from each other and formed one in each of the protrusions. This minimizes a risk of occurrence of leakage current between the contact springs or the connecting terminals arising from dew condensation and ensures a high degree of measurement accuracy of the gas sensor.

7 Claims, 13 Drawing Sheets

(51) Int. Cl.
 *H01R 13/508* (2006.01)
 *H01R 13/66* (2006.01)

(56) References Cited

U.S. PATENT DOCUMENTS

| | | | | |
|---|---|---|---|---|
| 2003/0024300 | A1* | 2/2003 | Kojima | G01N 27/4077 |
| | | | | 73/31.05 |
| 2007/0272431 | A1* | 11/2007 | Yamauchi | G01N 27/407 |
| | | | | 174/138 F |
| 2010/0139364 | A1 | 6/2010 | Kume et al. | |
| 2010/0139379 | A1* | 6/2010 | Kume | G01N 27/4062 |
| | | | | 73/114.73 |
| 2012/0006093 | A1 | 1/2012 | Yamada et al. | |

FOREIGN PATENT DOCUMENTS

| | | | | |
|---|---|---|---|---|
| JP | 2007-155517 | † | 6/2007 | |
| JP | 2010-101723 | | 5/2010 | |
| JP | 2011-133350 | † | 7/2011 | |
| JP | 2011-133351 | | 7/2011 | |
| JP | 2011133350 A | * | 7/2011 | |
| JP | 2013-515961 | | 5/2013 | |
| JP | 2013-178228 | | 9/2013 | |

\* cited by examiner
† cited by third party

GAS SENSOR

CROSS REFERENCE TO RELATED DOCUMENT

The present application claims the benefit of priority of Japanese Patent Application No. 2016-250260 filed on Dec. 23, 2016 the disclosure of which is incorporated herein by reference.

BACKGROUND

1 Technical Field

The invention relates generally to a gas sensor engineered to measure exhaust gas that is a target to be measured.

2 Background Art

Gas sensors designed to measure exhaust gas emitted from an internal combustion engine typically include a sensor device, a housing, a lead cover, a contact-spring insulator, and contact springs. The sensor device work to measure the exhaust gas. The housing retains the sensor deice using a sensor insulator. The lead cover is secured to the housing. The contact-spring insulator retains contact springs therein. The spring contacts are placed in contact with electrical leads of electrodes affixed to the sensor device and electrical leads of a heater arranged on the sensor device. The spring contacts are connected through connecting terminals to electrical leads wired in an external control device located outside the gas sensor.

The lead cover often has formed therein inlet holes through which air used as a reference in measuring the gas in the sensor device is introduced from outside the gas sensor. A filter is arranged on the inlet holes which admits gas to pass therethrough, but blocks liquid. The air, having entered the head cover at the inlet holes with the filter, passes through a hole of the contact-spring insulator in which the contact springs are disposed and reaches the sensor device. Japanese Patent First Publication No. 2013-178228 discloses such a type of gas sensor.

Usually, conditions where gas sensors which measure the exhaust gas emitted from the internal combustion engine are used undergo a wide change in temperature resulting from a cyclic change in temperature of the internal combustion engine. Liquid water usually passes through the filter on the inlet holes of the lead cover, but water vapor, as produced from evaporation of the water at high temperatures, will pass through the filter and then enter the lead cover.

Gas sensors which are not equipped with the above type of a filter disposed on the inlet holes also have a risk that water vapor enters the lead cover. For instance, gas sensors with no inlet hole have a sealing mechanism which blocks the entrance of the exhaust gas also face a risk that the sealing mechanism cannot hermetically seal the lead cover completely, so that the exhaust gas enters the lead cover. Usually, electrical leads do not have a complete sealing structure and, thus, encounter a risk that air enters the lead cover.

The gas sensors which measure the exhaust gas are usually exposed to high temperatures and thus engineered to work at a temperature (e.g., hundreds of degrees) higher than a dew point at which water vapor will start being condensed. Usually, water vapor, having entered the lead cover, is drained without being condensed along the same path as when it enters the lead cover. A change in temperature of the gas sensor arising from splashing with rain, however, may cause the water vapor in the lead cover to become liquid.

The amount of the condensed water entering the lead cover is usually small. When the temperature temporarily has dropped and then returned back to a normal level, the condensed water in the lead cover will be evaporated again, so that the water vapor is discharged from the lead cover. The above publication, therefore, does not consider dew condensation.

However, in order to deal with exhaust emission regulations which will be more tightened, there is a need for eliminating electrical noise added to an output of the gas sensors to improve the accuracy of the sensor output. For example, in a case where NOx gas which is infinitesimally contained in the exhaust gas is measured by a gas sensor, an output current from the gas sensor is usually very small. Such a type of gas sensor, therefore, needs to minimize adverse effects of noise on the output of the gas sensor for enhancing the measurement accuracy thereof.

The gas sensor designed to measure NOx gas usually measures electrical current flowing between two electrodes disposed on a sensor device installed in the gas sensor. Therefore, when the condensed water simultaneously touches a contact spring and a connecting terminal electrically connected to one of the electrodes and a contact spring and a connecting terminal electrically connected to the other electrode, it will cause a small amount of leakage current to flow among them, which may generate noise impinging on the output of the gas sensor.

SUMMARY

It is an object of this disclosure to provide a gas sensor which is capable of minimizing the leakage current and has an enhanced accuracy in measuring gas.

According to one aspect of the invention, there is provided a gas sensor which comprises: (a) a sensor device which works to measure exhaust gas; (b) a plurality of contact springs which are placed in contact with the sensor device; (c) a contact-spring insulator which has formed therein a plurality of holding holes in which the contact springs are retained; (d) a plurality of connecting terminals which connect the contact springs with electrical leads; and (e) a lead cover which covers the contact-spring insulator and the connecting terminals. The lead cover has formed therein an inner chamber which includes a connecting-terminal chamber and a contact-spring chamber which are isolated from each other by the contact-spring insulator. The connecting-terminal chamber has the connecting terminals disposed therein. The contact-spring chamber has the sensor device and the contact springs disposed therein. The contact-spring insulator has a terminal-facing end surface which faces the connecting terminals and also includes as many lead-insertion-hole protrusions as the contact springs formed on the terminal-facing end surface. The contact-spring insulator has formed therein a plurality of through-holes each of which opens both at an end surface of one of the lead-insertion-hole protrusions and at an end surface of one of the holding holes. The through-holes have the respective contact springs passing therethrough. All the through-holes are discrete from each other and formed one in each of the lead-insertion-hole protrusions.

The gas sensor is designed to have a unique configuration of the terminal-facing end surface of the contact-spring insulator which retains the contact springs therein. The terminal-facing end surface faces the connecting terminals. Specifically, the terminal-facing end surface has formed thereon as many lead-insertion-hole protrusions as the contact springs, i.e., the through-holes. The terminal-facing end surface has, thus, formed thereon the recess defined by the lead-insertion-hole protrusions. The through-holes have the respective contact springs passing therethrough. All the through-holes are discrete from each other and formed one in each of the lead-insertion-hole protrusions. Each of the connecting terminals connecting with the contact springs is disposed in alignment with one of the lead-insertion-hole protrusions on the terminal-facing end surface.

The above structures of the lead-insertion-hole protrusions and the through-holes serve to minimize a risk that dew condensation water is generated in the connecting-terminal chamber of the lead cover, which causes leakage current to flow between the contact springs or the connecting terminals in the following way.

Specifically, the recess on the terminal-facing end surface occupies a gap between the adjacent the lead-insertion-hole protrusions. This prevents the dew condensation water on any of the lead-insertion-hole protrusions from expanding to the adjacent lead-insertion-hole protrusion(s). In other words, the dew condensation water on any one of the lead-insertion-hole protrusions stays thereon or is drained into the recess or the side surface of the contact-spring insulator subjecting mechanical vibration transmitted from an internal combustion engine or produced by motion of the vehicle. The draining of the dew condensation water into the recess prevents the dew condensation water from expanding over some of the lead-insertion-hole protrusions unless the recess is fully filled with the water.

The recess on the terminal-facing end surface has no through-hole formed therein, thereby avoiding simultaneous contact of droplets of the dew condensation water on the lead-insertion-hole protrusions between one of the contact springs or the connecting terminals and another of the contact springs or the connecting terminals, thereby eliminating the risk of the leakage current therebetween. This ensures the stability of the measuring operation of the gas sensor.

Each of the lead-insertion-hole protrusions is, as apparent from the above discussion, formed by a protrusion in which the single through-hole is formed. The terminal-facing end surface may also have an additional protrusion formed thereon other than the lead-insertion-hole protrusions.

The inner chamber of the lead cover is made up of the connecting-terminal chamber and the contact-spring chamber which are isolated from each other by the contact-spring insulator. This prevents the dew condensation water from flowing from the connecting-terminal chamber into the contact-spring chamber even when moisture in the connecting terminal chamber enters the contact-spring chamber through gaps between the contact springs and inner walls of the through-holes.

The above structure of the gas sensor is, therefore, capable of minimizing a risk of occurrence of the leakage current and ensuring a required degree of accuracy in the gas measuring operation of the gas sensor.

The gas sensor may be engineered to measure the concentration of oxygen contained in the exhaust gas emitted from the internal combustion engine as well as NOx or another gas component. The gas sensor may alternatively be designed for use in determining an air-fuel ratio in the internal combustion engine which is derived using the exhaust gas or determining whether an air-fuel ratio, as calculated using the exhaust gas, is on a rich or a lean side of the stoichiometric air-fuel ratio.

Symbols in brackets represent correspondence relation between terms in claims and terms described in embodiments which will be discussed later, but are not limited only to parts referred to in the disclosure.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
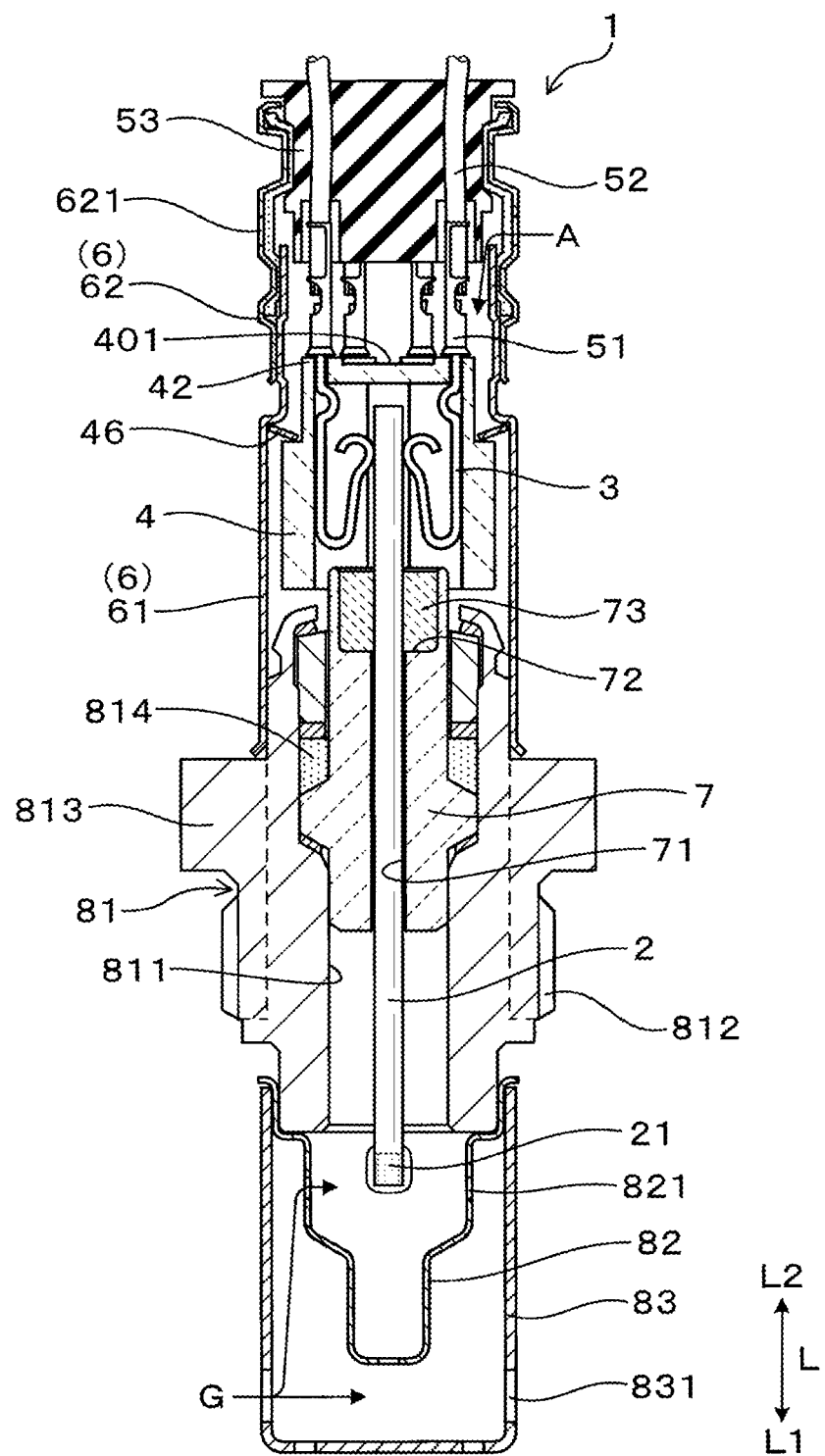
FIG. 1 is a sectional view which shows a gas sensor according to an embodiment.

Referring now to the drawings, particularly to FIG. 1, there is shown the gas sensor 1 according to an embodiment.

The gas sensor 1, as illustrated in FIG. 1, includes the sensor device 2, a plurality of contact springs 3, the contact-spring insulator 4, a plurality of connecting terminals 51, and the lead cover 6. The sensor device 2 works to measure exhaust gas G that is a target to be measured. The contact springs 3 are, as clearly illustrated in FIG. 2, placed in electrical contact with the electrode leads 222 disposed on the sensor device 2 to achieve an electrical connection of the sensor device 2 with an external control device. The contact-spring insulator 4 has formed therein the holding holes 41 in which the contact springs 3 are retained. The connecting terminals 51 are joined to electrical leads 52, respectively, which connect the contact springs 3 with the control device. The lead cover 6 covers the contact-spring insulator 4 and the connecting terminals 51.

Figure 2:
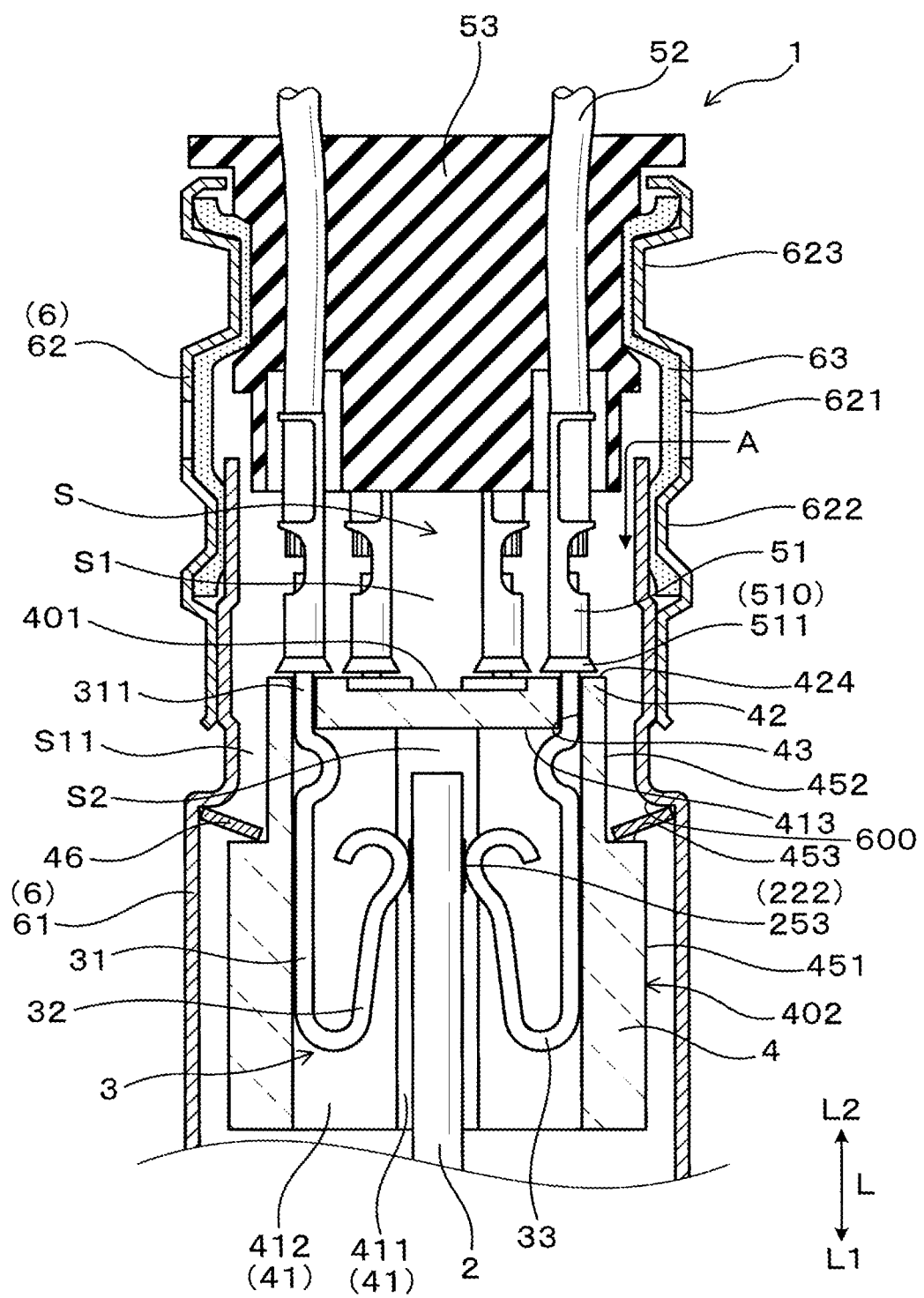
FIG. 2 is an enlarged view which illustrates a region around a contact-spring insulator installed in the gas sensor of FIG. 1.

The lead cover 6, as clearly illustrated in FIG. 2, has a space or inner chamber S formed therein. The inner chamber S is divided into the connecting-terminal chamber S1 and the contact-spring chamber S2 which are isolated from each other by the contact-spring insulator 4. The connecting-terminal chamber S1 has the connecting terminals 51 arranged therein. The contact-spring chamber S2 has the sensor device 2 and the contact springs 3 disposed therein. The connecting-terminal chamber S1 is designed to admit air A to enter from outside the gas sensor 1. The air A is used by the sensor device 2 as a reference gas in determining, for example, the concentration of NOx in the exhaust gas G. The air A in the connecting-terminal chamber S1 then flows into the contact-spring chamber S2.

Figure 3:
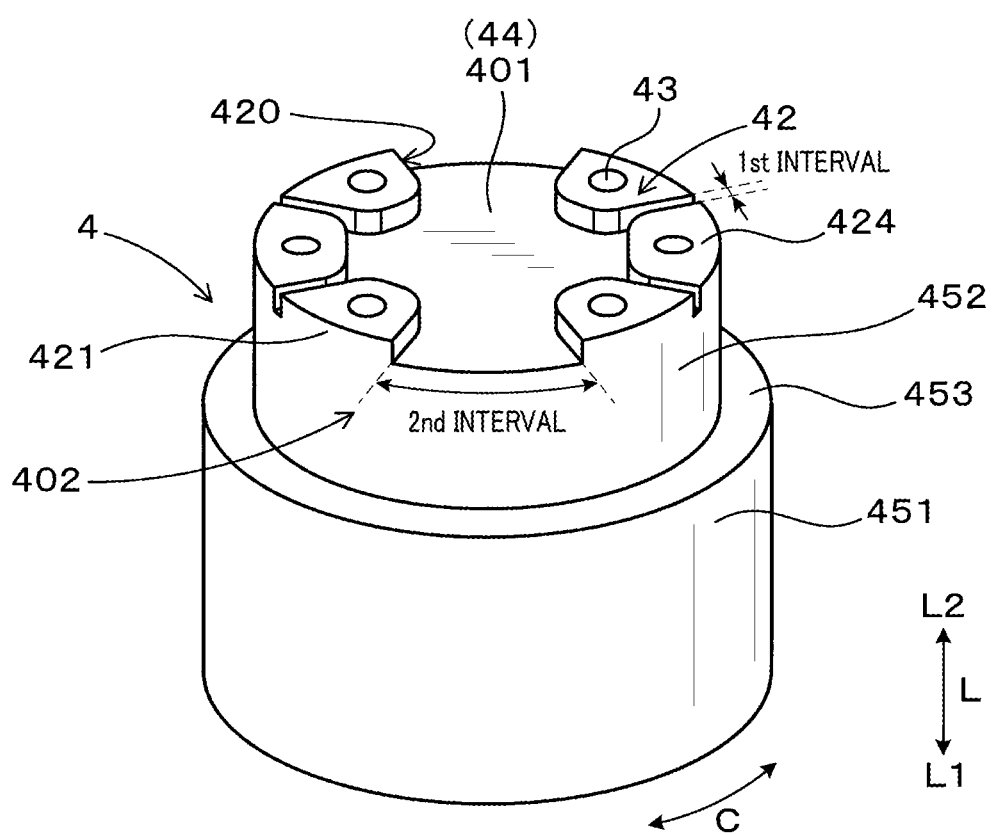
FIG. 3 is a perspective view which illustrates a contact-spring insulator in an embodiment.

The contact-spring insulator 4, as clearly illustrated in FIG. 3, has the circular end surface 401 facing the connecting terminals 51 (which will also be referred to as a terminal-facing end surface). The terminal-facing end surface 401 has formed thereon as many lead-insertion-hole protrusions 42 as the contact springs 3. The contact-spring insulator 4 has formed therein a plurality of through-holes 43 which open at the end surfaces 424 of the lead-insertion-hole protrusions 42 and the end surface 413 of the holding holes 41. The through-holes 43 have the contact springs 3 passing therethrough, respectively. Each of the through-holes 43 is formed in one of the lead-insertion-hole protrusions 42.

In this embodiment, a direction in which the sensor device 2 passes through the sensor-device insulator 7 will be referred to below as a sensor-extending direction L or a lengthwise direction of the sensor device 2. The sensor device 2 has a given length. A direction which extends along a longitudinal center line (i.e., an axis) of the sensor device 2 and perpendicular to the sensor-extending direction L will also be referred to below as a radial direction R. The sensor device 2 has a circumference. The circumferential direction of the sensor device 2 extending around the longitudinal center line of the gas sensor 2 will also be referred to as a circumferential direction C. The sensor device 2 includes the sensing portion 21 extending from a major body of the sensor device. A side of the gas sensor 1 in which the sensing portion 21 lies will also be referred to as a front end side L1, while an opposite side of the gas sensor 1 will also be referred to as a rear end side L2. A direction in which a front end (i.e., the sensing portion 21) of the sensor device 2 faces the front end (i.e., a lower end in FIG. 1) of the gas sensor 1 will also be referred to as a frontal direction L1, while an opposite direction will also be referred to as a rearward direction L2.

The gas sensor 1 of this embodiment will be described below in detail.

Internal Combustion Engine

The gas sensor 1 is installed in a pipe (e.g., an exhaust pipe) of an exhaust system of an internal combustion engine mounted in a vehicle and works to measure or sense oxygen or a predetermined gas component contained in the exhaust gas G flowing in the pipe. The gas sensor 1 may be arranged either upstream or downstream of a catalyst mounted in the pipe. The pipe in which the gas sensor 1 is mounted may be either a pipe connecting with an inlet of a supercharger which is powered by the exhaust gas G and works to increase the density of air supplied to the internal combustion engine or a pipe installed in an exhaust gas recirculation mechanism which recirculate a portion of the exhaust gas G, as emitted from the internal combustion engine into an exhaust pipe, back into an intake path leading to the internal combustion engine.

The vehicle equipped with the pipe in which the gas sensor 1 is mounted is a typical vehicle powered by fuel, a vehicle equipped with an idle-stop system (also called an automatic engine stop/restart system) which works to stop the idling of the engine when the vehicle is stopped, or a hybrid vehicle. The gas sensor 1 may be engineered to measure the concentration of oxygen contained in the exhaust gas G emitted from the internal combustion engine as well as NOx or another gas component. The gas sensor 1 may alternatively be designed for use in determining an air-fuel ratio in the internal combustion engine which is derived using the exhaust gas G or determining whether an air-fuel ratio, as calculated using the exhaust gas G, is on a rich or a lean side of the stoichiometric air-fuel ratio.

Sensor Device 2

Figure 4:
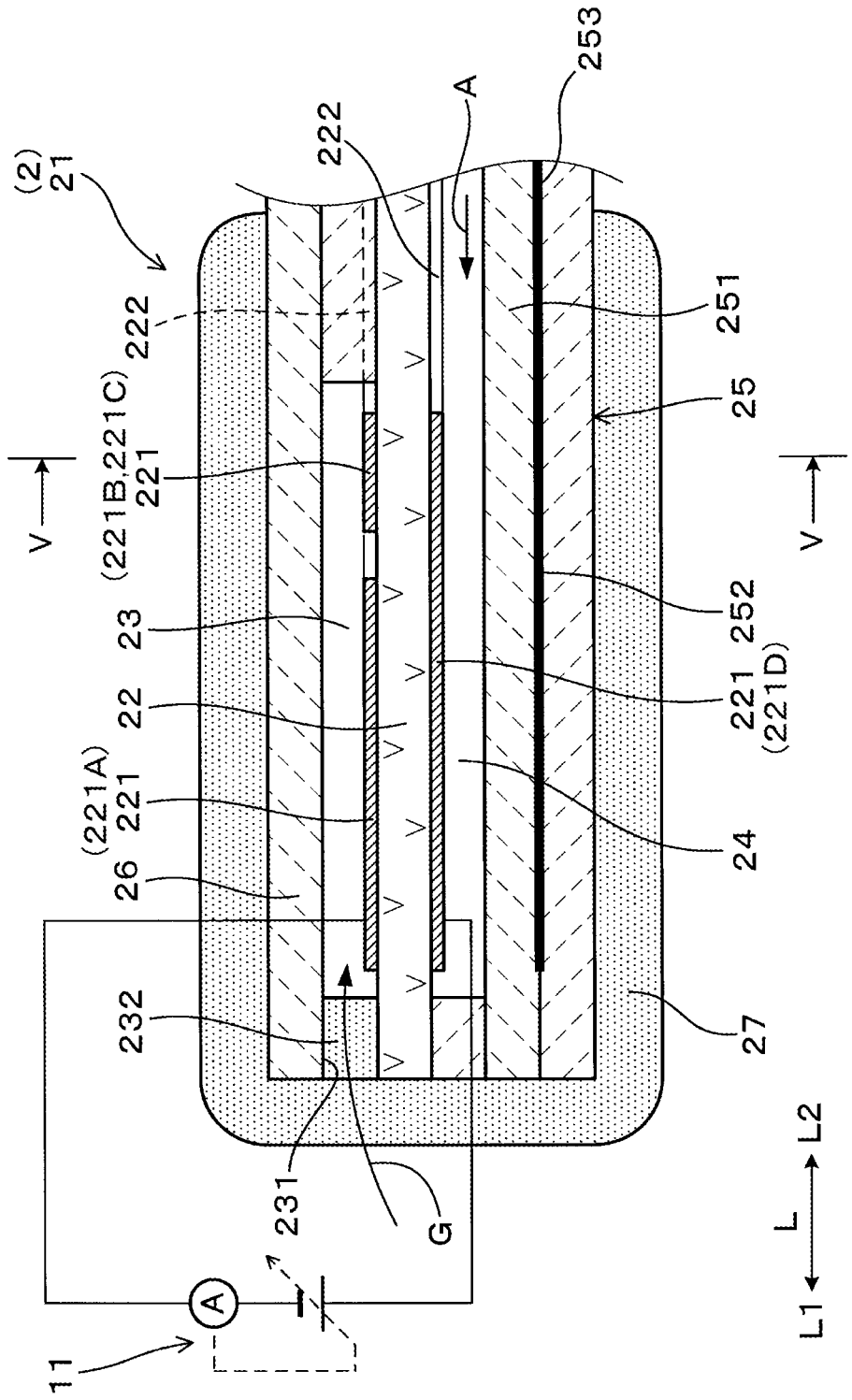
FIG. 4 is a sectional view which illustrates a sensor device installed in the gas sensor of FIG. 1.
Figure 5:
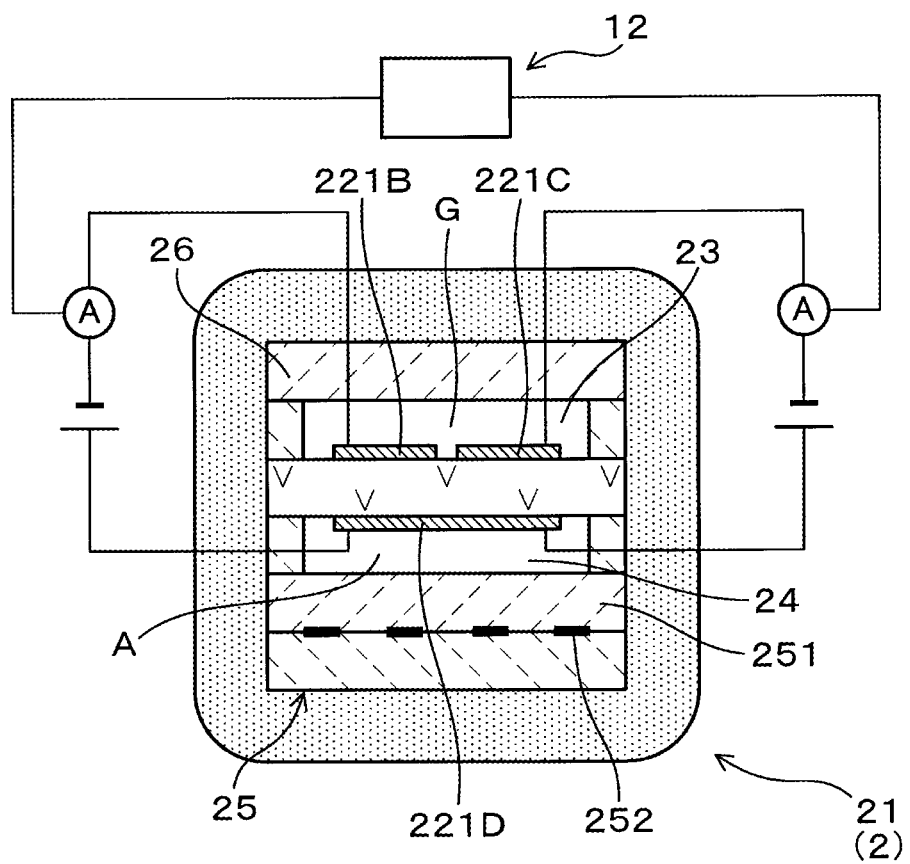
FIG. 5 is a sectional view, as taken along the line V-V in FIG. 4.

The sensor device 2, as illustrated in FIGS. 4 and 5, includes the solid electrolyte body 22 and electrodes 221A, 221B, 221C, and 221D (which will be generally denoted by 221) formed on opposed major surfaces of the solid electrolyte body 22. The solid electrolyte body 22 has an ion-conductivity which achieves conduction of oxide ions therein when the solid electrode body 22 is at a given activation temperature. The sensor device 2 is made of a stack of the plate-like solid electrolyte body 22 and the heater 25 disposed on the solid electrolyte body 22. The sensor device 2 may alternatively be, as clearly illustrated in FIG. 6, of a cup-shape and have the bar-shaped heater 25 disposed inside the cup-shaped solid electrolyte body 22. In this case, the electrodes 221A and 221D are affixed to an inner peripheral surface and an outer peripheral surface of the solid electrolyte body 22.

Figure 6:
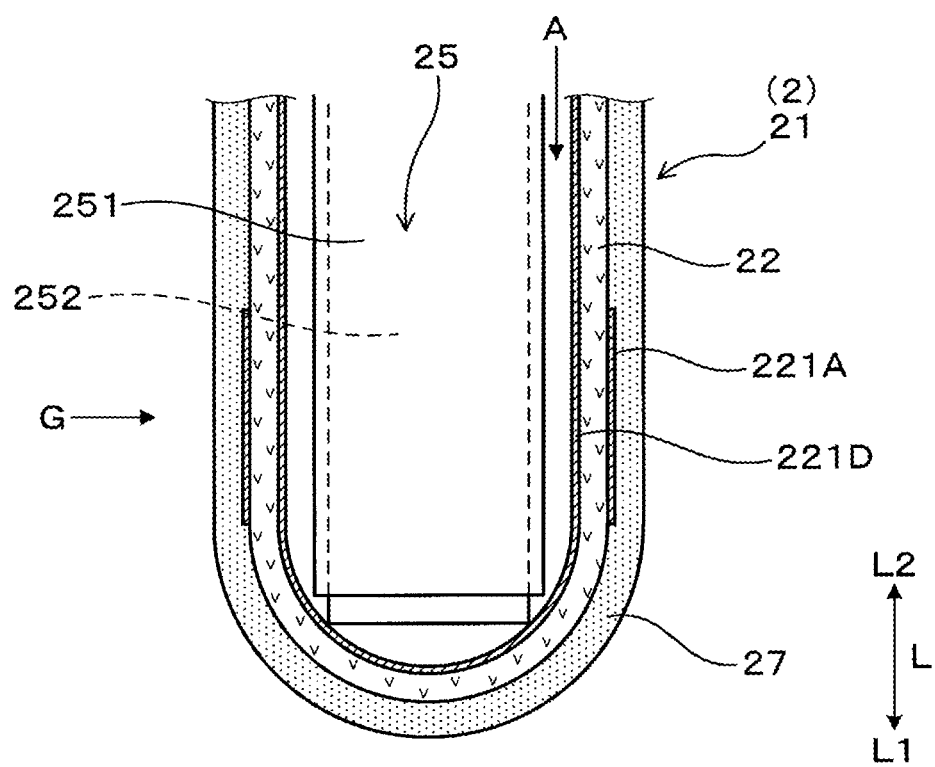
FIG. 6 is a sectional view which shows a modification of a sensor device which may be used with the gas sensor of FIG. 1.

The sensor device 2 is, as illustrated in FIGS. 4 to 6, equipped with the sensing portion 21 which contacts with the exhaust gas G. Specifically, the sensing portion 21 in this embodiment is designed to measure NOx (Nitrogen Oxide), which will also be referred to as a given gas component), contained in the exhaust gas G emitted from the internal combustion engine. The air A, as already described, is used as a reference gas in determining, for example, the concentration of NOx in the exhaust gas G. The solid electrolyte body 22 of the planar sensor device 2 has two major surfaces opposed to each other. The electrodes 221A, 221B, and 221C are disposed on an outer one of the major surfaces of the solid electrolyte body 22 and exposed directly to the exhaust gas G. The electrode 221D is affixed to the other major surface (i.e., an inner surface) of the solid electrolyte body 22 and directly exposed to the air A. The heater 25 of the sensor device 2 includes the ceramic substrate 251 and the heating element 252 affixed to the ceramic substrate 251. The heating element 252 is supplied with electrical power to produce heat.

The sensor device 2, as can be seen in FIGS. 1 and 4, has a length which passes through the sensor-device insulator 7 and extends in the sensor-extending direction L. The sensing portion 21 is disposed on a front end of the sensor device 2 which is located on the front end side L1. The sensing portion 21 may be arranged on a portion of the sensor device 2 near the front end. The sensor device 2 has a rear end which is located on the rear end side L2 and on which the electrode leads 222 connecting with the electrodes 221 and the heating element leads 253 connecting with the heating element 252 are disposed.

The sensing portion 21 is, as illustrated in FIG. 4, made of portions of the sensor device 2 on which the electrodes 221A, 221B, 221C, and 221D are arranged. The electrodes 221A, 221B, and 221C which contact with the exhaust gas G are exposed to the gas chamber 23 enclosed by the insulating ceramic substrate 26 disposed on the solid electrolyte body 22. The gas chamber 23 communicates with the gas inlet 231 in which the diffusion resistance layer 232 is disposed. The diffusion resistance layer 232 produces a given degree of resistance to which a flow of the exhaust gas G is subjected while passing through the diffusion resistance layer 232, in other words, serves to produce a flow of the exhaust gas G at a given diffusion velocity when entering the gas chamber 23. The front end portion (i.e., the front end side L1) of the sensor device 2 including the sensing portion 21 is covered with the protective layer 27. The diffusion resistance layer 232 and the protective layer 27 are each made of a porous ceramic material. The sensor device 2 has formed therein the duct 24 which directs the air A to the electrode 221D. The duct 24 extends in the sensor-extending direction L from the rear end thereof which faces the rear end (i.e., the rear end side L2) of the gas sensor 1 to a portion of the sensing portion 21 on which the electrode 221D is arranged.

The electrodes 221A, 221B, and 221C which are, as illustrated in FIGS. 4 and 5, exposed to the exhaust gas G function as a pump electrode, a sensor electrode, and a monitor electrode, respectively. The pump electrode 221A works to decompose oxygen molecules in the exhaust gas G to control the concentration of oxygen in the exhaust gas G. The sensor electrode 221B works to decompose NOx and oxygen molecules remaining in the exhaust gas G after the concentration of oxygen in the exhaust gas G is controlled by the pump electrode 221A. The monitor electrode 221C works to decompose oxygen molecules remaining in the exhaust gas G after the concentration of oxygen in the exhaust gas G is controlled by the pump electrode 221A. The electrode 221D which is exposed to the air A functions as a reference electrode is laid to overlap with the pump electrode 221A, the sensor electrode 221B, and the monitor electrode 221C in the thickness-wise direction of the solid electrolyte body 22. In other words, the reference electrode 221D is shared by the pump electrode 221A, the sensor electrode 221B, and the monitor electrode 221C. The reference electrode 221D exposed to the air A may alternatively be discrete electrodes each of which faces a respective one of the pump electrode 221A, the sensor electrode 221B, and the monitor electrode 221C in the thickness-wise direction of the solid electrolyte body 22.

The gas sensor 1 is connected to a controller which includes the voltage applying circuit 11 and the detecting circuit 12. The voltage applying circuit 11 works to apply voltage between the pump electrode 221A and the reference electrode 221D. The detecting circuit 12 works to detect a difference between an electrical current flowing between the sensor electrode 221B and the reference electrode 221D and an electrical current flowing between the monitor electrode 221C and the reference electrode 221D. Specifically, the detecting circuit 12 subtracts the electrical current flowing between the monitor electrode 221C and the reference electrode 221D from that flowing between the sensor electrode 221B and the reference electrode 221D to determine the concentration of NOx from which an error arising from the residual oxygen is eliminated. The monitor electrode 221C may be omitted.

Figure 7:
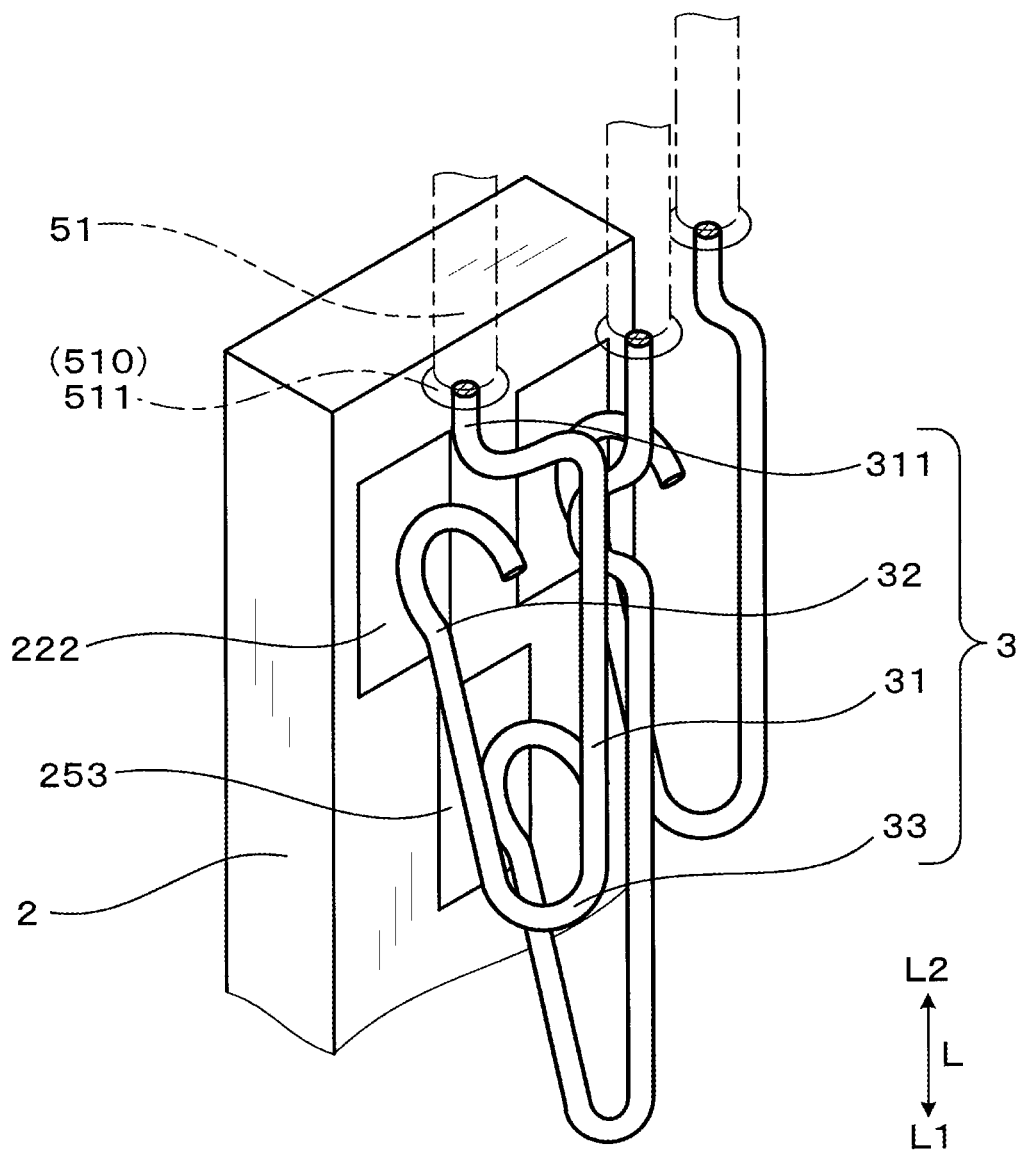
FIG. 7 is a perspective view which illustrates contact springs placed in contact with a sensor device according to an embodiment.

The sensor device 2, as clearly illustrated in FIG. 7, has four electrode leads 222 which are formed on the rear end portion thereof (i.e., the rear end side L2) and connect with the pump electrode 221A, the sensor electrode 221B, the monitor electrode 221C, and the reference electrode 221D, respectively. The sensor device 2 also has two heating element leads 253 (only one is shown for the brevity of illustration) attached to the rear end portion thereof. The heating element leads 253 connect with ends of the heating element 252. Specifically, the two electrode leads 222 and the one heating element lead 253 are affixed to each of the major opposed surfaces of the sensor device 2. The total of four electrode leads 222 and the total of two heating element leads 253 may be arranged in any pattern on the opposed surfaces of the sensor device 2.

Modification of Sensor Device 2

Figure 8:
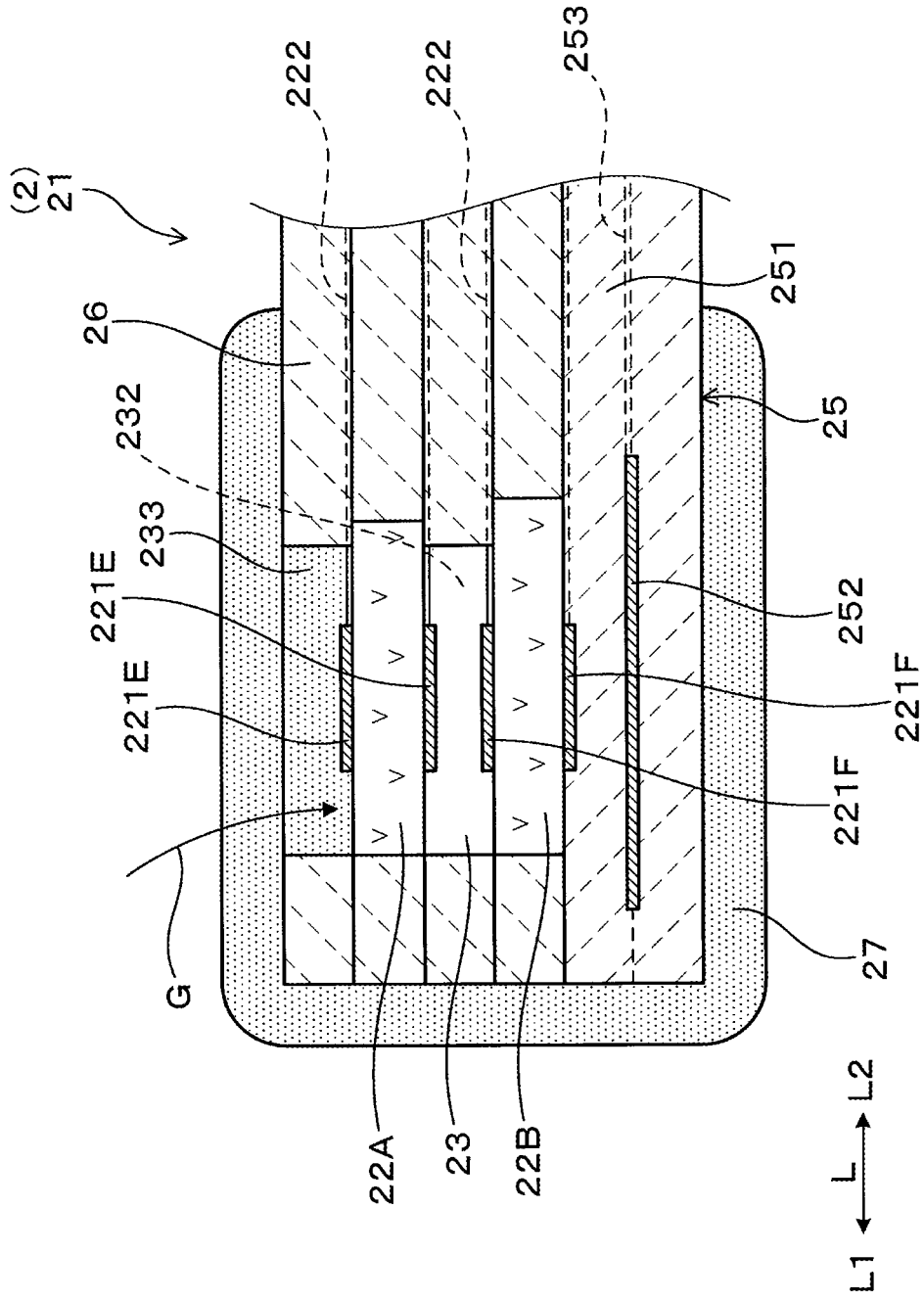
FIG. 8 is a sectional view which illustrates a modification of a sensor device.

The sensor device 2 may be designed to have a structure illustrated in FIG. 8. Specifically, the sensor device 2 is made up of two solid electrolyte bodies 22A and 22B on which pairs of electrodes 221E and electrodes 221F are disposed, respectively. The solid electrolyte bodies 22A and 22B have formed therebetween the gas chamber 23 into which the exhaust gas G is introduced. The gas chamber 23 is enclosed by the insulating ceramic substrate 26. The first solid electrolyte body 22A has two opposed major surfaces on which the pump electrodes 221E are disposed to control the concentration of oxygen in the exhaust gas G within the gas chamber 23. The pump electrodes 221E are opposed to each other in the thickness-wise direction of the first solid electrolyte body 22. One of the pump electrodes 221E is exposed directly to the gas chamber 23, while the other pump electrode 221E is embedded in the gas inlet layer 223 which is made of a porous material through which the exhaust gas G penetrates.

The second solid electrolyte body 22B has two opposed major surfaces on which the sensor electrodes 221F are disposed to measure the concentration of oxygen in the exhaust gas G within the gas chamber 23. The sensor electrodes 221F are opposed to each other in the thickness-wise direction of the second solid electrolyte body 22B. One of the sensor electrodes 221F is arranged within the gas chamber 23, while the other sensor electrode 221F is embedded in the ceramic substrate 251. The sensor electrodes 221F and a portion of the second solid electrolyte body 22B located between the sensor electrodes 221F form a sensor cell working to measure the concentration of oxygen. The diffusion resistance layer 232 is arranged adjacent the gas chamber 23. The diffusion resistance layer 232 produces a flow of the exhaust gas G delivered at a given diffusion velocity into the gas chamber 23. The heater 25 is disposed on the solid electrolyte body 22B. The heater 25 includes the ceramic substrate 251 and the heating element 252 mounted in the ceramic substrate 251. The heating element 252 is supplied with electric power to generate heat.

Sensor-Device Insulator 7

Referring back to FIG. 1, the sensor-device insulator 7 is made of an insulating ceramic, also called an insulating porcelain. The sensor-device insulator 7 has formed therein the mount hole 71 which extends through the sensor-device insulator 7 in the sensor-extending direction L and in which the sensor device 2 is mounted. The sensor device 2 passes through the mount hole 71 and is firmly retained by the glass member 73 in the sensor-device insulator 7. The glass member 73 is fit in the recess 72 formed in the rear end of the sensor insulator 7 in communication with the mount hole 71.

Housing 81

The gas sensor 1, as illustrated in FIG. 1, includes the housing 81. The housing has formed therein the housing hole 811 which extends through the housing 81 in the sensor-extending direction L and in which the sensor-device insulator 7 is disposed. The sensor-device insulator 7 extends through the housing hole 811 and is firmly retained inside the housing hole 811 through the sealing member 814, such as talc powder or a sleeve, by inwardly bending or crimping the rear end of the housing 81. The sealing member 814 is disposed in a rear portion of the housing hole 811 on the rear end side L2. The housing 81 has the flange 813 and the external thread 812 formed on an entire outer circumferential surface thereof. The flange 813 and the thread 812 achieve a firm joint of the gas sensor 1 in a mount hole formed in a pipe (e.g., the exhaust pipe, as described above).

Contact Spring 3

Figure 9:
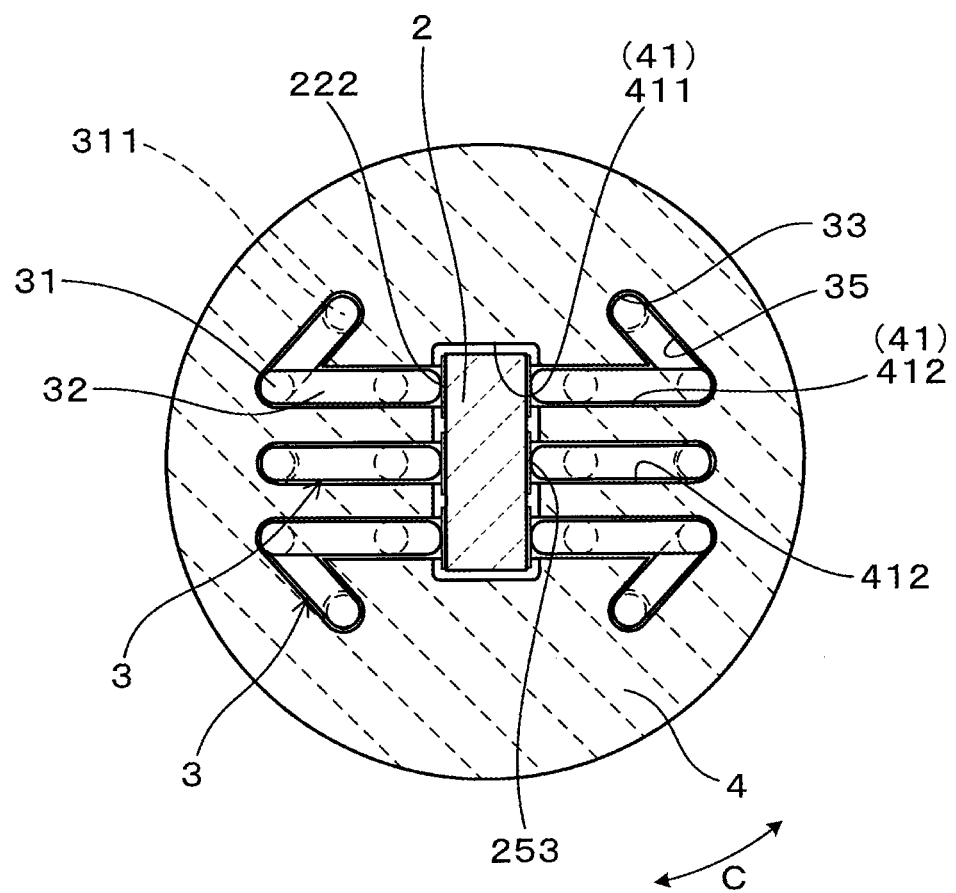
FIG. 9 is a sectional view which illustrates a contact-spring insulator in which a sensor device and contact springs are disposed in an embodiment, as viewed from a side where the contact springs are inserted into the contact-spring insulator.

The contact-spring insulator 4, as illustrated in FIGS. 2 and 9, holds therein the six contact springs 3 which contacts the four electrode leads 222 and the two heating element leads 253. Each of the contact springs 3 includes the spring body 31, the spring contact 32, and the bend 33 connecting between the spring body 31 and the contact spring 32. The spring body 31 is disposed in one of the holding holes 41 of the contact-spring insulator 4. The spring contact 32 is bent from the spring body 31 and contacts a corresponding one of the electrode leads 222 and the heating element leads 253. The spring contact 32 is elastically deformed within the holding hole 41. Similarly, the bend 33 is also elastically deformed in the holding hole 41. The elastic deformation of the spring contact 32 and the bend 33 serve to produce elastic restorative force which urges the spring contact 32 into constant contact with a corresponding one of the electrode leads 222 and the heating element leads 253. The rear end of the sensor device 2 in the sensor-extending direction L is held by all of the contact-springs 3. Specifically, every two of the contact-springs 3 which face each other, as can be seen in FIG. 9, hold the rear end of the sensor device 2 therebetween.

The spring body 31 of each of the contact springs 3, as clearly illustrated in FIG. 2, includes the extension portion 311 extending from the rear end (i.e., the rear end side L2) of the spring body 31 in the sensor-extending direction L. The extension portion 311 passes through one of the through-holes 43 of the contact-spring insulator 4. The extension portion 311 has a rear end protruding from the terminal-facing end surface 401 of the contact-spring insulator 4 in the sensor-extending direction L toward the rear end (i.e., the rear end side L2) of the gas sensor 1. The extension portion 311 is joined to a corresponding one of the connecting terminals 51 which extend in the sensor-extending direction L and face the terminal-facing end surface 401. Each of the contact springs 3 is made of steel wire which is circular in a cross section thereof and bent into the illustrated shape. The use of the circular wire ensures a required degree of mechanical strength of the contact springs 3 and enables the distance along which the contact springs 3 are arranged in the circumferential direction C of the contact-spring insulator 4, in other words, an interval between respective adjacent two of the contact springs 3 to be minimized. In this embodiment the six contact springs 3 are mounted in the contact-spring insulator 4. It is, thus, useful to minimize such a distance in the circumferential direction C.

The contact springs 3 may alternatively be shaped to have an oval or a polygonal transverse cross section. The contact-spring insulator 4 may alternatively have the less than or more than six contact springs 3 retained therein. In the case where the number of the electrodes used with the sensor device 2 is increased, the number of the contact springs 3 may be increased accordingly.

Contact-Spring Insulator 4

The contact-spring insulator 4 is, as illustrated in FIGS. 2 and 9, made of an insulating ceramic, also called insulating porcelain. The contact-spring insulator 4 is laid to overlap the rear end of the sensor-device insulator 7 in the sensor-extending direction L, in other words, in alignment with the sensor-device insulator 7 in the lengthwise direction of the gas sensor 1. The holding holes 41 of the contact-spring insulator 4 include the sensor-device mounting hole 411 in which the sensor device 2 is disposed and the six spring holding holes 412 in which the six contact springs 3 are mounted, respectively, and which communicate with the sensor-device mounting hole 411. The sensor-device mounting hole 411 and the spring holding holes 412 extend from the front end to the rear end of the contact-spring insulator 4 in the sensor-extending direction L.

The contact-spring insulator 4, as can be seen in FIG. 3, has a circular circumferential surface that is a side surface extending parallel to the sensor-extending direction L. In other words, the contact-spring insulator 4 has a circular traverse cross section. The terminal-facing end surface 401 of the contact-spring insulator 4 forms a rear end surface of the contact-spring insulator 4 facing the rear end side L2 of the gas sensor 1 in the sensor-extending direction. In this embodiment, the contact-spring insulator 4 has the six lead-insertion-hole protrusions 42, one for each of the six contact springs 3. The lead-insertion-hole protrusions 42 are formed on the terminal-facing end surface 401 and face the rear end of the gas sensor 1 in the sensor-extending direction L.

Figure 10:
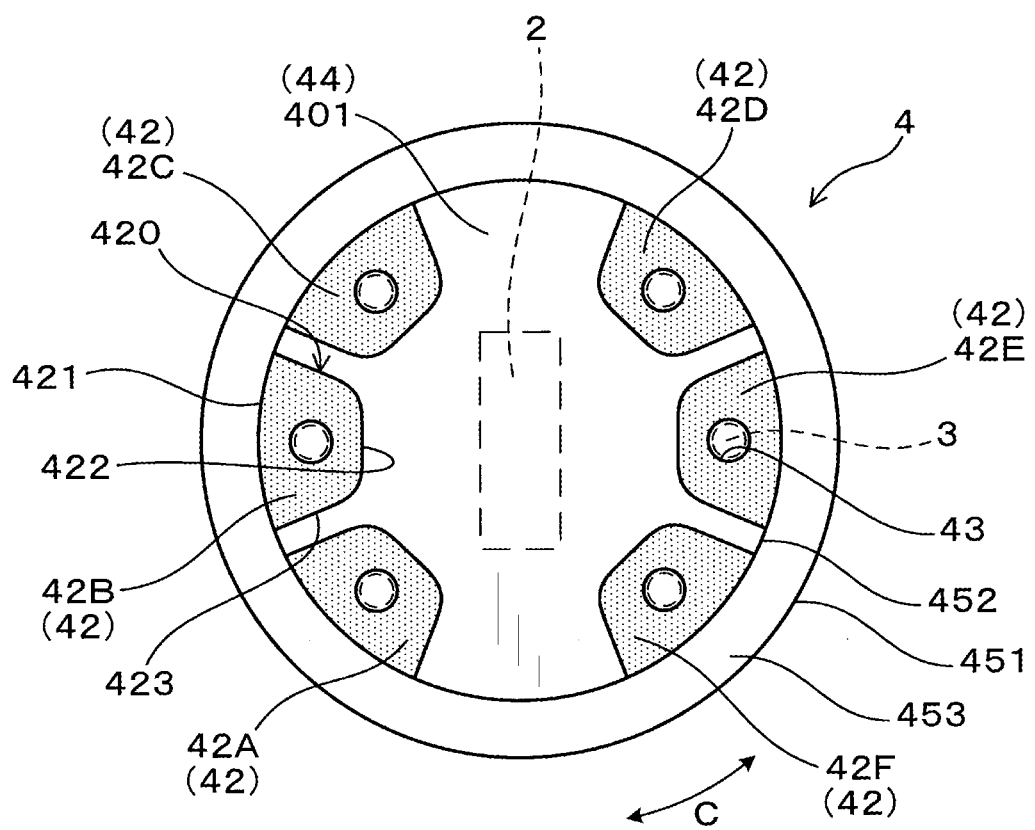
FIG. 10 is a sectional view which illustrates a contact-spring insulator in an embodiment, as viewed from a direction opposite a direction in which contact springs are inserted into the contact-spring insulator.

As viewed from the rear end side L2 of the gas sensor 1 in the sensor-extending direction L, the lead-insertion hole protrusions 42 are broken into two groups: a first group and a second group on the terminal-facing end surface 401. Specifically, three (i.e. a half) of the lead-insertion hole protrusions 42 are collected to form each of the first and second groups. The first group is on the left side on the terminal-facing end surface 401, as viewed in FIG. 3, while the second group is on the right side on the terminal-facing end surface 401. If the six lead-insertion-hole protrusions 42 are, as illustrated in FIG. 10, numbered in serial order clockwise in the circumferential direction C of the contact-spring insulator 4 as the first lead-insertion-hole 42A to sixth lead-insertion hole 42F, every two of the first lead-insertion-hole protrusion 42A to the third lead-insertion-hole protrusion 42C (i.e., the first group) are arranged at a first interval away from each other in the circumferential direction C of the contact-spring insulator 4. Similarly, every two of the fourth lead-insertion-hole protrusion 42D to the sixth lead-insertion-hole protrusion 42F (i.e., the second group) are arranged at the first interval (which is identical with that in the first group) away from each other in the circumferential direction C of the contact-spring insulator 4. The third lead-insertion-hole protrusions 42C and the fourth lead-insertion-hole protrusions 42D are arranged at a second interval away from each other in the circumferential direction C of the contact-spring insulator 4. Similarly, the sixth lead-insertion-hole protrusions 42F and the first lead-insertion-hole protrusions 42A are arranged at the second interval (which is identical with that between the third lead-insertion-hole protrusions 42C and the fourth lead-insertion-hole protrusions 42D) away from each other in the circumferential direction C of the contact-spring insulator 4. The first interval is set shorter than the second interval in the circumferential direction C of the contact-spring insulator 4.

The first interval is selected in consideration of a predictable or expected maximum quantity of dew condensation water generated in the connecting-terminal chamber S1 of the lead cover 6. For instance, the first interval is determined to be more than or equal to 0.5 mm. When the first interval is less than 0.5 mm, it will cause the dew condensation water to hardly flow down from the lead-insertion-hole protrusions 42. Specifically, the contact-spring insulator 4, as clearly illustrated in FIG. 3, has the recess 44 defined by the lead-insertion-hole protrusions 42 on the terminal-facing end surface 401. The first interval which is less than 0.5 mm will result in a difficulty for the dew condensation water, as generated on the lead-insertion-hole protrusions 42, to drain to the recess 44. In order to desirably reduce the size of the contact-spring insulator 4, the first interval may be selected to be less than or equal to 5.0 mm. All the lead-insertion-hole protrusions 42 may alternatively be arranged at equal intervals away from each other on the terminal-facing end surface 401 in the circumferential direction C in favor of reducing the size of the contact-spring insulator 4.

The lead-insertion-hole protrusions 42 are, as clearly illustrated in FIG. 3, located in an outer circumferential area of the terminal-facing end surface 401 in the radial direction R of the contact-spring insulator 4. Specifically, each of the lead-insertion-hole protrusions 42 has the side or peripheral surface 420. Each of the peripheral surfaces 420 includes an outer peripheral surface (which will also be referred to below as an outer side surface) 421 which faces outwardly in the radial direction R of the contact-spring insulator 4. The outer peripheral surfaces 421 of all of the lead-insertion-hole protrusions 42 are laid flush with the outer circumferential surface (i.e., a side surface) 402 of the contact-spring insulator 4. In other words, the outer peripheral surfaces 421 of all of the lead-insertion-hole protrusions 42 form portions of the outer circumferential surface 402 of the contact-spring insulator 4.

The outer peripheral surfaces 421 of the lead-insertion-hole protrusions 42 and the outer circumferential surface 402 of the contact-spring insulator 4 form a single peripheral surface, in other words, they are aligned with each other in the sensor-extending direction L, thereby causing the quantity of dew condensation water draining from the lead-insertion-hole protrusions 42 onto the outer circumferential surface 402 of the contact-spring insulator 4 to be greater than that draining from the lead-insertion-hole protrusions 42 into the recess 44. This results in a decrease in quantity of water accumulated on the terminal-facing end surface 401, thereby keeping the dew condensation water away from the connecting terminals 51 and thus minimizing a risk that the leakage current is generated among the connecting terminals 51.

The alignment of the outer peripheral surfaces 421 with the outer circumferential surface 402 also results in decreased stepped portions of the contact-spring insulator 4, thereby minimizing burrs which are protrusions usually formed when the stepped portions are machined in production processes of the contact-spring insulator 4. It is usually difficult in the production process to cast ceramic material into a mold used in forming corners of the stepped portions of the contact-spring insulator 4, which may lead to cracks in the corners of the stepped portions. A decrease in number of the stepped portions is, therefore, useful in ensuring a desired configuration and quality of the contact-spring insulator 4.

The contact-spring insulator 4 may alternatively be shaped to have at least one of the outer peripheral surfaces 421 of the lead-insertion-hole protrusions 42 which is laid flush with the outer circumferential surface 402 of the contact-spring insulator 4. This arrangement also offers the advantages that the dew condensation water is drained onto the outer circumferential surface 402 to minimize the leakage current in the sensor device 2, and there is a decreased risk that the burrs or cracks are formed on or in the contact-spring insulator 4.

Figure 11:
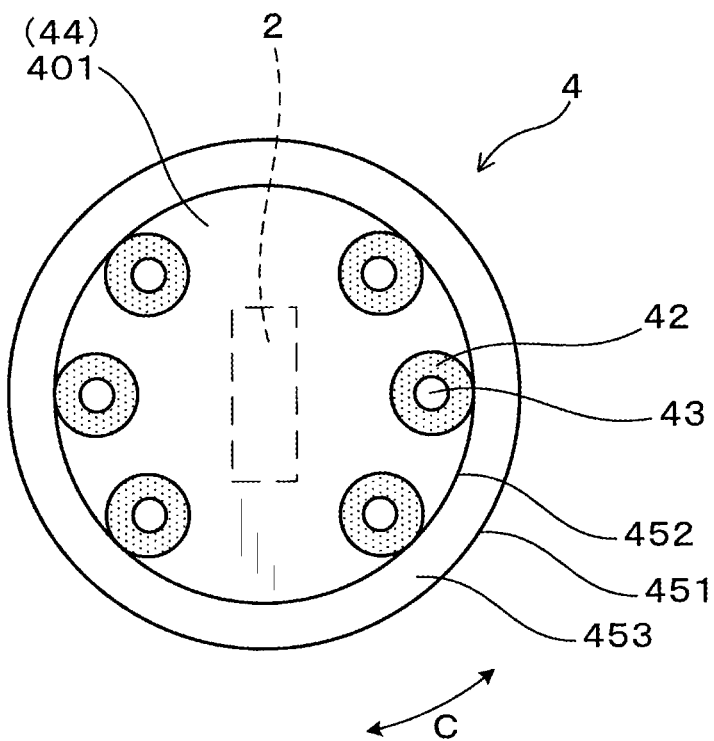
FIG. 11 is a sectional view which illustrates a modification of a contact-spring insulator, as viewed from a direction opposite a direction in which contact springs are inserted into the contact-spring insulator.
Figure 12:
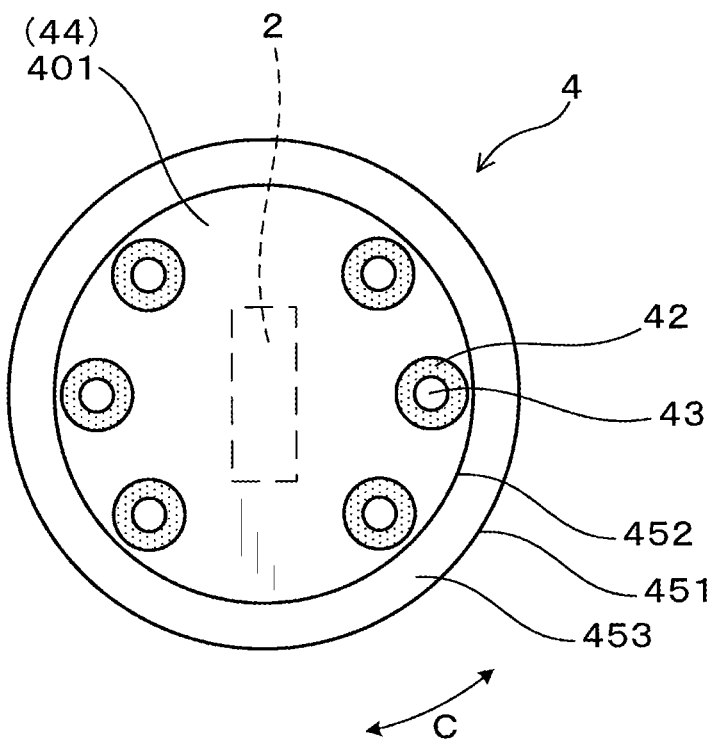
FIG. 12 is a sectional view which illustrates a modification of a contact-spring insulator, as viewed from a direction opposite a direction in which contact springs are inserted into the contact-spring insulator.

As viewed from the rear end side L2 of the gas sensor 1 in the sensor-extending direction L, the peripheral surface 420 of each of the lead-insertion-hole protrusions 42, as illustrated in FIG. 10, includes the inner side surface 422 which faces inwardly in the radial direction R of the contact-spring insulator 4. The inner side surface 422 may be of either a straight, i.e., flat shape or a curved, i.e., arc shape. Additionally, the peripheral surface 420 of each of the lead-insertion-hole protrusions 42 also includes a pair of side surfaces 423 continuing from the inner side surface 422. The side surfaces 423 of each of the lead-insertion-hole protrusions 42 are geometrically oriented to have a given interval therebetween in the circumferential direction C of the contact-spring insulator 4. The interval, as can be seen in FIG. 10, increases from the inner side surface 422 toward the outer peripheral surface 421. The peripheral surface 420 of each of the lead-insertion-hole protrusions 42 may alternatively be formed, as illustrated in FIGS. 11 and 12, in a circular shape whose center lies at the center of a corresponding one of the through-holes 43, as viewed from the rear end side L2 of the gas sensor 1 in the sensor-extending direction L. In this case, each of the outer peripheral surfaces 421 may be shaped to have an outer portion which, as illustrated in FIG. 11, lies flush with the outer circumferential surface 402 of the contact-spring insulator 4 or, as illustrated in FIG. 12, extends in misalignment with the outer circumferential surface 402 of the contact-spring insulator 4 in the sensor-extending direction L.

Figure 13:
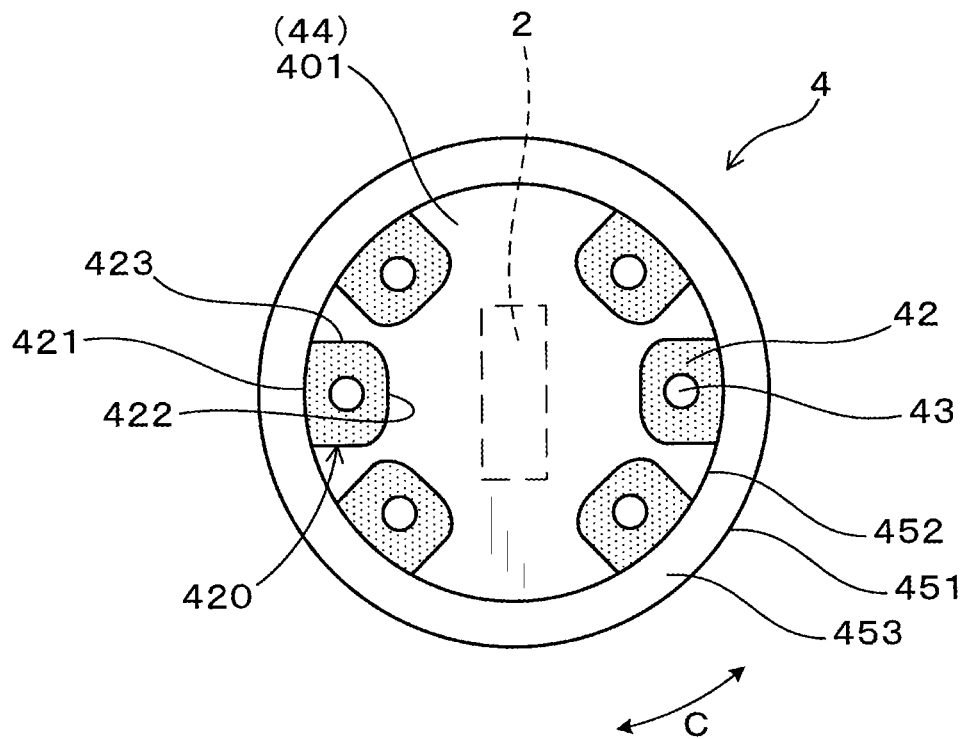
FIG. 13 is a sectional view which illustrates a modification of a contact-spring insulator, as viewed from a direction opposite a direction in which contact springs are inserted into the contact-spring insulator.
Figure 14:
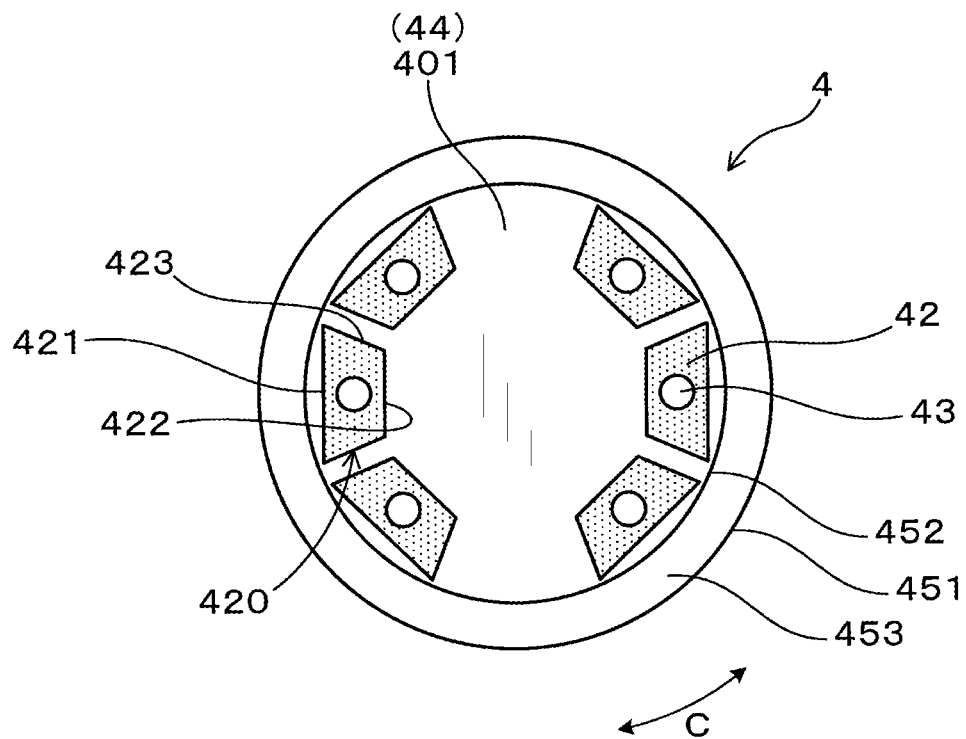
FIG. 14 is a sectional view which illustrates a modification of a contact-spring insulator, as viewed from a direction opposite a direction in which contact springs are inserted into the contact-spring insulator.

The peripheral surface 420 of each of the lead-insertion-hole protrusions 42 may alternatively be shaped, as illustrated in FIG. 13, to have the side surfaces 423 which lead to the inner side surface 422 and extend parallel to each other, as viewed from the rear end side L2 of the gas sensor 1 in the sensor-extending direction L. The outer peripheral surface 421, the inner side surface 422, and the side surfaces 432 leading to the outer peripheral surface 421 and the inner side surface 422 may alternatively be, as illustrated in FIG. 14, shaped to extend straight, but not be curved, as viewed from the rear end side L2 of the gas sensor 1 in the sensor-extending direction L.

Figure 15:
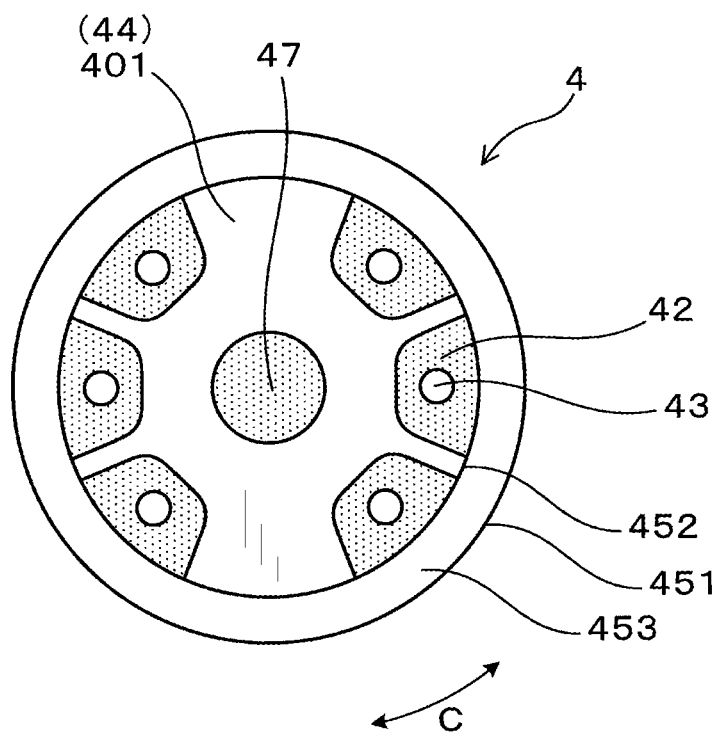
FIG. 15 is a sectional view which illustrates a modification of a contact-spring insulator, as viewed from a direction opposite a direction in which contact springs are inserted into the contact-spring insulator.
Figure 16:
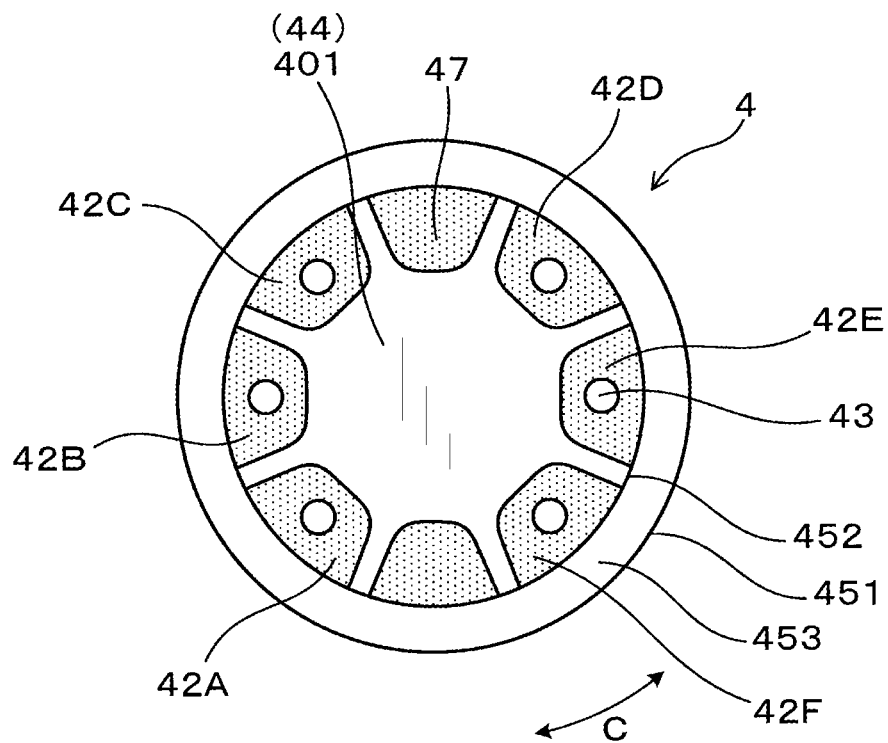
FIG. 16 is a sectional view which illustrates a modification of a contact-spring insulator, as viewed from a direction opposite a direction in which contact springs are inserted into the contact-spring insulator.

The contact-spring insulator 4 may alternatively be formed to have a configuration shown in either FIG. 15 or 16. Specifically, the contact-spring insulator 4 in FIG. 15 has an additional protrusion 47 on the terminal-facing end surface 401 which is located away from the lead-insertion-hole protrusions 42. For instance, the protrusion 47 lies at the center of the terminal-facing end surface 401 inside the lead-insertion-hole protrusions 42 in the radial direction R of the contact-spring insulator 4. The contact-spring insulator 4 in FIG. 16 has two additional protrusions 47 arranged between the third and fourth lead-insertion-hole protrusions 42C and 42D and between the sixth and first lead-insertion-hole protrusions 42F and 42A in the circumferential direction C of the contact-spring insulator 4.

Referring back to FIGS. 2 and 3, the contact-spring insulator 4 includes a small-diameter portion and a large-diameter portion which are aligned in the sensor-extending direction L. The large-diameter portion extends from the small-diameter portion through the outer shoulder 453 and is located farther away the rear end side L2 in the sensor-extending direction L than the small-diameter portion is. The large-diameter portion has the first outer peripheral surface 451, while the small-diameter portion has the second outer peripheral surface 452. In other words, the outer circumferential surface 402 of the contact-spring insulator 4 includes the first outer peripheral surface 451 and the second outer peripheral surface 452 which continue from each other through the shoulder 453. The first outer peripheral surface 451 has a diameter larger than that of the second outer peripheral surface 452. The disc spring 46 is, as clearly illustrated in FIG. 2, disposed on the shoulder 453 between the first outer peripheral surface 451 and the second outer peripheral surface 452. The contact-spring insulator 4 is retained inside the lead cover 6 through the disc spring 46 disposed between the shoulder 453 and the inner shoulder 600 of the lead cover 6. When pressed in the sensor-extending direction L, the disc spring 46 produces an elastic restorative force.

Depending on a structure which retains the contact-spring insulator 4 in the lead cover 6, the outer circumferential surface 402 of the contact-spring insulator 4 may be formed not to have the shoulder 453, but shaped to extend as a whole parallel in the sensor-extending direction L or be inclined at a given angle (excluding zero) to the sensor-extending direction L. In this case, the retaining of the contact-spring insulator 4 in the lead cover 6 may be achieved by pressing an outer peripheral portion of the terminal-facing end surface 401 of the contact-spring insulator 4 using the disc spring 46.

Each of the lead-insertion-hole protrusions 42, as illustrated in FIG. 3, has the rear end surface 424 which faces the rear end side L2 of the gas sensor 1 in the sensor-extending direction L. The rear end surface 424 is shaped to be flat. The terminal-facing end surface 401 has a flat area other than areas in which the lead-insertion-hole protrusions 42 are formed. The flat portion defines the recess 44. Specifically, the whole of the area of the terminal-facing end surface 401 other than the areas occupied by the lead-insertion-hole protrusions 42 forms the recess 44 (i.e., the flat bottom of the recess 44). The area of the terminal-facing end surface 401 other than the areas occupied by the lead-insertion-hole protrusions 42 has formed therein no through-hole communicating with the holding holes 41. The terminal-facing end surface 401 may alternatively be shaped to have formed therein at least one additional recess which does not extend through the contact-spring insulator 4 or at least one protrusion.

The recess 44 of the terminal-facing end surface 401 may have small irregularities, dimples, hollows, or protrusions. The rear end surface 424 of each of the lead-insertion-hole protrusions 42 which faces the rear end side L2 of the gas sensor 1 in the sensor-extending direction L may be curved or rounded. The peripheral surface 420 of each of the lead-insertion-hole protrusions 42 extends parallel in the sensor-extending direction L, but may alternatively be inclined at a given angle to the sensor-extending direction L.

The distance between the rear end surface 424 (i.e., the top end surface) of each of the lead-insertion-hole protrusions 42 and the terminal-facing end surface 401, in other words, the height of each of the lead-insertion-hole protrusions 42 in the sensor-extending direction L may be selected to be 0.4 mm or more. The height of each of the lead-insertion-hole protrusions 42 may be selected to be 1.5 mm or less in order to avoid oversizing of the contact-spring insulator 4. In this embodiment, the height of the lead-insertion-hole protrusions 42 from the terminal-facing end surface 401 are the same, but may alternatively be different from each other.

The six through-holes 43 are formed in the rear surface (i.e., the rear end side L2) of the contact-spring insulator 4 and extend in the sensor-extending direction L to establish communication of the lead-insertion-hole protrusions 42 with the spring holding holes 412 or the sensor-device mounting hole 411, respectively. Each of the through-holes 43 opens at both the rear end surface 424 of a corresponding one of the lead-insertion-hole protrusions 42 and the front end surface 413 of the contact-spring insulator 4. The front end surface 413 is, as can be seen in FIG. 2, an inner surface (i.e., a bottom surface) of a rear end wall of the contact-spring insulator 4. The inner surface faces the front end side L1. In other words, the through-holes 43 extend through the thickness of the rear end wall of the contact-spring insulator 4. Each of the through-holes 43 is circular in a transverse cross section thereof, but may alternatively be shaped to have a polygonal or an oval transverse cross section.

Connecting Terminal 51

The connecting terminals 51, as can be seen in FIG. 2, each serve as a joint sleeve or an electrical connector which electrically connect conductive layers of the electrical leads 52 with the extension portions 311 of the spring bodies 31 of the contact springs 3, respectively. Each of the connecting terminals 51 is of a hollow cylindrical shape. Each of the connecting terminals 51 has a rear end which faces the rear end side L2 of the gas sensor 1 in the sensor-extending direction L, in which the conductive layer of a corresponding one of the electrical leads 52 is disposed, and which is elastically crimped to achieve a firm electrical joint therebetween. Each of the connecting terminals 51 has a front end which faces the front end side L1 of the gas sensor 1 in the sensor-extending direction L, in which the extension portion 311 of a corresponding one of the contact springs 3, and which is elastically crimped to achieve a firm electrical joint therebetween. The electrical leads 52 to which the connecting terminals 51 are joined are disposed in the control device. Each of the electrical leads 52 is made up of a resinous electrical insulating layer and a length of wire or conductive layer disposed in the insulating layer.

This embodiment is designed to have a unique relation between the size of the through-holes 43 and the size of the terminal ends 510 of the connecting terminals 51 which face the front end side L1 of the gas sensor 1 in the sensor-extending direction L. Specifically, the terminal end 510 of each of the connecting terminals 51 is equipped with the cover 511 which is of a frusto-conical shape and tapers toward the rear end side L2 of the connecting terminal 51. In other words, the cover 511 is shaped to have a diameter increasing toward the front end side L1 of the gas sensor 1 in the sensor-extending direction L. The conical cover 511 of each of the connecting terminals 51 which face the terminal-facing end surface 401 has a minimum diameter which is greater than a maximum diameter of the through-holes 43.

The through-holes 43 are shaped to have a circular transverse section. Similarly, the covers 511 are shaped to have a circular transverse section. The cover 511 of each of the connecting terminals 51 has a front end which directly faces the through-hole 53 in the sensor-extending direction L and has an outer diameter greater than an inner diameter of the through-holes 43. For instance, the outer diameter of the front end of the cover 511 is set greater than the inner diameter of the through-hole 43 by 0.5 mm to 4 mm. The covers 511 and the through-holes 43 may alternatively be shaped to have a polygonal or an oval transverse section. In this disclosure, a minimum dimension (e.g., a minimum outer diameter) of the transverse section of the cover 511 is also referred to as a minimum external dimension. A maximum dimension (e.g., a maximum inner diameter) of the traverse section of the through-hole 43 is also referred to as a maximum internal dimension.

Each of the through-holes 4 has an opening in the terminal-facing end surface 401 is enclosed or covered with the cover 511 of the terminal end 510 of a corresponding one of the connecting terminals 51. When dew condensation water is produced inside the connecting-terminal chamber S1 of the lead cover 6, the cover 511 serves to receive the dew condensation water and blocks the entrance of the dew condensation water into the through-hole 43. An air gap is created between the opening of each of the through-holes 43 and the cover 511 of a corresponding one of the connecting terminals 51 for admitting the air A to pass therethrough.

Lead Cover 6

The lead cover 6, as illustrated in FIG. 2, has a front end portion which faces the front end side L1 of the gas sensor 1 in the sensor-extending direction L and is fit on an outer periphery of a rear end portion of the housing 81 which faces the rear end side L2 in the sensor-extending direction L. The lead cover 6 is made of a combination of the first cover 61 and the second cover 62 which are arranged in alignment with each other. The first cover 61 is fit on an outer circumference of the housing 81. The second cover 62 is fit on an outer circumference of a rear end portion of the first cover 61 which faces the rear end side L2 of the gas sensor 1 in the sensor-extending direction L. The second cover 62 has formed therein air inlet holes 621 through which the air A is delivered into the connecting-terminal chamber S1 of the lead cover 6. The filter 63 made of porous sheet is wrapped around an inner periphery of the second cover 62. The filter 63 covers the air inlet holes 621 and admits air to pass therethrough, but blocks a flow of liquid therethrough.

The second cover 62 has the rubber-made bush 53 fit in the inner periphery thereof to hermetically close a rear opening of the second cover 62 facing the rear end side L2 in the sensor-extending direction L. The bush 53 retains the electrical leads 52 therein. The second cover 62 has two crimped portions 622 and 623 which are arranged away from each other in the sensor-extending direction L. The crimped portion 622 which is located closer to the front end side L1 than the crimped portion 623 is in the sensor-extending direction L is formed by inwardly crimping a portion of the circumference of the second cover 62 to firmly retain the filter 62 between the first cover 61 and the second cover 62. The crimped portion 623 which is located closer to the rear end side L2 than the crimped portion 622 is in the sensor-extending direction L is formed by inwardly crimping a portion of the circumference of the second cover 62 to elastically deform the bush 53, thereby retaining the electrical leads 52 in the bush 53. The crimped portion 623 also holds the filter 63 between the second cover 62 and the bush 53.

Inner Cover 82 and Outer Cover 83

The gas sensor 1 also includes, as illustrated in FIG. 1, a cover assembly made up of the inner cover 82 and the outer cover 83. The inner cover 82 is fit on an outer circumference of a front end of the housing 81 which faces the front end side L1 in the sensor-extending direction L. The inner cover 82 extends from the front end of the housing 81 toward the front end side L1 of the gas sensor 1 and covers the sensing portion 21 of the sensor device 2. The outer cover 83 surrounds the whole of the inner cover 82. The inner cover 82 and the outer cover 83 defines therebetween the gas flow path 830 through which the exhaust gas G flows. The inner cover 82 has formed therein the inner pass holes 821 through which the exhaust gas G passes. The outer cover 83 has formed therein the outer pass holes 831 through which the exhaust gas G passes.

Inner Chamber S in Lead Cover 6

The contact-spring insulator 4 is, as clearly illustrated in FIGS. 1 and 2, retained in the lead cover 6 using the disc spring 46 placed on the shoulder 453 of the contact-spring insulator 4. The inner chamber S in the lead cover 6 is divided by the contact-spring insulator 4 and the disc spring 46 into the connecting-terminal chamber S1 and the contact-spring chamber S2 which are isolated from each other. The connecting-terminal chamber S1 is enclosed by the contact-spring insulator 4, the disc spring 46, the lead cover 6, and the bush 53. The contact-spring chamber S2 is enclosed by the contact-spring insulator 4, the disc spring 46, the lead cover 6, the housing 81, and the sensor-device insulator 7.

The connecting-terminal chamber S1 is, as illustrated in FIG. 2, also exposed to the circumference of the second outer peripheral surface 452 of the contact-spring insulator 4 which is located closer to the rear end side L2 of the contact-spring insulator 4 in the sensor-extending direction L. The connecting-terminal chamber S1 includes an annular chamber S11 defined around the circumference of the second outer peripheral surface 452. The recess 44 on the terminal-facing end surface 401 of the contact-spring insulator 4, as illustrated in FIG. 3, also extend to the outer circumferential edge of the terminal-facing end surface 401 through the interval between adjacent two of the lead-insertion-hole protrusions 42. The recess 44 continues to or communicates with the outer circumference of the second outer peripheral surface 452. In other words, the recess 44 has a plurality of flow paths each of which is defined between adjacent two of the lead-insertion-hole protrusions 42 and opens at the outer circumference of the second outer peripheral surface 452.

The above configuration of the connecting-terminal chamber S1 works to drain the dew condensation water from the recess 44 on the terminal-facing end surface 401 into the annular chamber S11. Specifically, the dew condensation water accumulated on the lead-insertion-hole protrusions 42 is emitted directly into the annular chamber S11, thereby causing the dew condensation water to be accumulated in the annular chamber S11, thereby minimizing the quantity of the dew condensation water remaining in the recess 44.

In the gas sensor 1 of this embodiment, the connecting-terminal chamber S1 and the contact-spring chamber S2 communicate with each other only through air gaps in the through-holes 43 of the contact-spring insulator 4. In other words, the terminal-facing end surface 401 of the contact-spring insulator 4 does not have any through-hole other than the through-holes 43. The disc spring 46 which is disposed on the shoulder 453 of the outer circumferential surface 402 of the contact-spring insulator 4 hermetically isolates between the inner circumferential surface of the first cover 61 of the lead cover 6 and the outer circumferential surface 402 of the contact-spring insulator 4. This minimizes the entrance of dew condensation water, as generated in the connecting-terminal chamber S1, into the contact-spring chamber S2.

Beneficial Advantage

The gas sensor 1 of this embodiment is, as described already, designed to have a unique configuration of the terminal-facing end surface 401 of the contact-spring insulator 4 which retains a plurality of contact springs 3 therein. The terminal-facing end surface 401 faces a plurality of connecting terminals 51. Specifically, the terminal-facing end surface 401 has formed thereon as many lead-insertion-hole protrusions 42 as the contact springs 3, i.e., the through-holes 43. In this embodiment, there are six contact springs 3. The terminal-facing end surface 401 has, thus, formed thereon the six lead-insertion-hole protrusions 42 which are separate or discrete from each other. The lead-insertion-hole protrusions 42 form the recess 44 on the terminal-facing end surface 401. The recess 44 defines a water chamber which includes, as described above, the flow paths each radially extending between adjacent two of the lead-insertion-hole protrusions 42 and reaching the outer circumferential edge of the terminal-facing end surface 401. The recess 44 (i.e., the water chamber) has not through-hole extending from the terminal-facing end surface 401 to the contact-spring chamber S2 through the through-holes 43.

The air A, as delivered from the air inlet holes 621 of the lead cover 6 into the connecting-terminal chamber S1 of the lead cover 6 through the filter 63, usually contain moisture. Accordingly, when the gas sensor 1 is splashed with water, so that the air A in the connecting-terminal chamber S1 is cooled, it may cause the moisture in the connecting-terminal chamber S1 to be condensed, which generates dew condensation water. Usually, the thermal conductivity of the metallic connecting terminals 51 is higher than that of the ceramic contact-spring insulator 4, so that the dew condensation is easily generated on the connecting terminals 51.

The dew condensation water, occurring on the connecting terminals 51, may be accumulated on the lead-insertion-hole protrusions 42 facing the connecting terminals 51. The lead-insertion-hole protrusions 42 are, as described above, separate from each other, thereby facilitating the ease with which the dew condensation water is drained from each of the lead-insertion-hole protrusions 42 into the recess 44 or the second outer peripheral surface 452 of the contact-spring insulator 4.

The recess 44, as described above, includes flow paths each formed between the adjacent lead-insertion-hole protrusions 42, thereby minimizing a probability that the dew condensation water lies over some of the lead-insertion-hole protrusions 42. In other words, the dew condensation water on any one of the lead-insertion-hole protrusions 42 stays thereon or is drained into the recess 44 or the second outer peripheral surface 452 subjecting mechanical vibration transmitted from the internal combustion engine or produced by motion of the vehicle. The dew condensation water drained into the recess 44 is subjected to vibration and then easily emitted to the second outer peripheral surface 452. This minimizes the probability that the dew condensation water is accumulated over the adjacent the lead-insertion-hole protrusions 42.

The dew condensation water, as drained onto the second outer peripheral surface 452, is accumulated in the annular chamber S11 defined around the second outer peripheral surface 452, thereby avoiding accumulation of the dew condensation water on the connecting terminals 51.

The through-holes 43 are formed one in each of the lead-insertion-hole protrusions 42. The contact springs 3 are disposed one in each of the through-holes 43. The connecting terminals 51 connecting with the contact springs 3 face or are disposed in alignment with the lead-insertion-hole protrusions 42 arranged on the terminal-facing end surface 401, respectively, in the lengthwise direction of the gas sensor 1. The layout of the lead-insertion-hole protrusions 42, as described above, prevents the dew condensation water from lying over the adjacent lead-insertion-hole protrusions 42.

The above structure of the contact-spring insulator 4 avoids simultaneous contact of droplets of the dew condensation water on the lead-insertion-hole protrusions 42 between one of the contact springs 3 or the connecting terminals 51 and another of the contact springs 3 or the connecting terminals 51, thereby eliminating the risk of the leakage current therebetween. This ensures the stability of the measuring operation of the gas sensor 1.

The inner chamber S in the lead cover 6 includes the connecting-terminal chamber S1 and the contact-spring chamber S2 which are hermetically isolated by the contact-spring insulator 4 and the disc spring 46 from each other. The cover 511 of each of the connecting terminals 51 is arranged above a corresponding one of the openings of the through-holes 43 lying on the terminal-facing end surface 401, thereby causing the dew condensation water, as generated in the connecting-terminal chamber S1, to be received by the covers 511 to eliminate a risk that the dew condensation water flows into the through-holes 43.

The air gap through which the air A is admitted to pass is created between each of the covers 511 of the connecting terminals and the rear end surface 424 of a corresponding one of the lead-insertion-hole protrusions 42 The air A, as delivered from the air inlet holes 621 of the lead cover 6 into the connecting-terminal chamber S1 through the filter 63, therefore, passes through the air gaps between the covers 511 and the rear end surfaces 424 of the lead-insertion-hole protrusions 42 and the air gaps between the contact springs 3 and the through-holes 43 and then enters the contact-spring chamber S2. Subsequently, the air A is then introduced from the rear end of the sensor device 2 arranged in the contact-spring chamber S2 into the duct 24 of the sensor device 2, so that the air A is used in measuring the concentration of NOx in the sensor device 2.

As apparent from the above discussion, the gas sensor 1 of this embodiment serves to minimize the risk of the occurrence of the leakage current and ensure a required degree of accuracy in the gas measuring operation of the gas sensor 1.

Even if the gas sensor 1 is designed not to have the air inlet holes 621 with the filter 63, there is a risk that moisture, as having entered the lead cover 6, is changed into dew condensation water. This takes place, for example, when the sealing mechanism of the gas sensor 1 to block the entrance of the exhaust gas or the air sealing mechanism of the bush 53 to block the entrance of the air A has failed. In such an event, the above configuration of the contact-spring insulator 4 minimizes the risk of the occurrence of the leakage current and ensures a required degree of accuracy in the gas measuring operation of the gas sensor 1.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiment which can be embodied without departing from the principle of the invention as set forth in the appended claims.

What is claimed is:

1. A gas sensor comprising:
a sensor device which works to measure exhaust gas;
a plurality of contact springs which are placed in contact with the sensor device;
a contact-spring insulator which has formed therein a plurality of holding holes in which the contact springs are retained;
a plurality of connecting terminals which connect the contact springs with electrical leads; and
a lead cover which covers the contact-spring insulator and the connecting terminals,
wherein the lead cover has formed therein a chamber which includes a connecting-terminal chamber and a contact-spring chamber which are isolated from each other by the contact-spring insulator, the connecting-terminal chamber having the connecting terminals disposed therein, the contact-spring chamber having the sensor device and the contact springs disposed therein,
wherein the contact-spring insulator has a terminal-facing end surface which faces the connecting terminals and also includes as many lead-insertion-hole protrusions as the contact springs formed on the terminal-facing end surface,
wherein the contact-spring insulator has formed therein a plurality of through-holes each of which opens both at an end surface of one of the lead-insertion-hole protrusions and at an end surface of one of the holding holes, the through-holes having the contact springs passing therethrough, respectively,
wherein all the through-holes are discrete from each other and formed one in each of the lead-insertion-hole protrusions, and
wherein at least one of the lead-insertion-hole protrusions is arranged away from a first adjacent one of the lead-insertion-hole protrusions in a first circumferential direction by a first interval and the at least one of the lead-insertion-hole protrusions is arranged away from a second adjacent one of the lead-insertion-hole protrusions in a second circumferential direction opposite to the first circumferential direction by a second interval, and the first interval has a different distance than the second interval.

2. A gas sensor as set forth in claim 1, wherein the terminal-facing end surface has a flat area other than areas occupied by the lead-insertion-hole protrusions.

3. A gas sensor as set forth in claim 1, wherein each of the connecting terminals has a terminal end which faces the terminal-facing end surface and has a minimum external dimension greater than a maximum internal dimension of the through-holes, and wherein each of the through-holes has an opening which is formed in the terminal-facing end surface and covered with the terminal end of a corresponding one of the connecting terminals.

4. A gas sensor as set forth in claim 1, wherein each of all the lead-insertion-hole protrusions has a side surface which partially lies flush with a side surface of the contact-spring insulator.

5. A gas sensor as set forth in claim 1, wherein the terminal-facing end surface of the contact-spring insulator has no through-hole other than said through-holes, the side surface of the contact-spring insulator has an outer shoulder, and wherein the side surface of the contact-spring insulator and an inner peripheral surface of the lead cover are closed by a disc spring disposed on the outer shoulder over a circumferential direction of the contact-spring insulator.

6. A gas sensor as set forth in claim 1, wherein the lead-insertion-hole protrusions includes a first group of lead-insertion-hole protrusions and a second group of lead-insertion-hole protrusions, each of the lead-insertion-hole protrusions in the first group being separated from an adjacent one of the lead-insertion-hole protrusions in the first group by the first interval, each of the lead-insertion-hole protrusions in the second group being separated from an adjacent one of the lead-insertion-hole protrusions in the second group by the first interval, and the first group being separate from the second group by the second interval.

7. A gas sensor as set forth in claim 6, wherein the first interval is shorter than the second interval.

* * * * *